United States Patent
Biegelsen et al.

(10) Patent No.: US 9,675,296 B1
(45) Date of Patent: Jun. 13, 2017

(54) PULSATILE VENOUS BLOOD STOPPAGE FOR ANALYTE DETECTION

(71) Applicant: Verily Life Sciences LLC, Mountain View, CA (US)

(72) Inventors: David K. Biegelsen, Portola Valley, CA (US); Alex Hegyi, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 309 days.

(21) Appl. No.: 14/261,180

(22) Filed: Apr. 24, 2014

(51) Int. Cl.
  *A61B 5/1455* (2006.01)
  *A61B 5/00* (2006.01)
  *A61B 5/145* (2006.01)

(52) U.S. Cl.
  CPC ............ *A61B 5/6838* (2013.01); *A61B 5/145* (2013.01)

(58) Field of Classification Search
  None
  See application file for complete search history.

(56) References Cited

U.S. PATENT DOCUMENTS

| | | | |
|---|---|---|---|
| 5,450,858 A * | 9/1995 | Zablotsky | A61F 5/012 128/876 |
| 6,749,567 B2 | 6/2004 | Davis | |
| 8,137,698 B2 | 3/2012 | Peyman | |
| 8,481,082 B2 | 7/2013 | Peyman | |
| 8,571,623 B2 | 10/2013 | Baker | |
| 8,668,935 B2 | 3/2014 | Peyman | |
| 8,709,488 B2 | 4/2014 | Peyman | |
| 8,795,251 B2 | 8/2014 | Peyman | |
| 8,801,690 B2 | 8/2014 | Peyman | |
| 8,808,268 B2 | 8/2014 | Peyman | |
| 8,932,636 B2 | 1/2015 | Peyman | |
| 9,017,729 B2 | 4/2015 | Peyman | |
| 2012/0214175 A1 | 8/2012 | Graham | |
| 2013/0197330 A1 | 8/2013 | Al-Ali | |
| 2013/0231574 A1 | 9/2013 | Tran | |
| 2014/0114152 A1* | 4/2014 | Fournier | A61B 5/02116 600/324 |

* cited by examiner

*Primary Examiner* — Eric Winakur
*Assistant Examiner* — Marjan Fardanesh
(74) *Attorney, Agent, or Firm* — McDonnell Boehnen Hulbert & Berghoff LLP

(57) ABSTRACT

A wearable device includes a mount configured to mount the wearable device to an external body surface proximate to a vessel, a downstream clamp configured to apply a force to the vessel sufficient to inhibit a flow of fluid through the vessel beyond the downstream clamp, and an upstream clamp, positioned upstream of the downstream clamp, configured to apply a force to the vessel sufficient to accelerate a volume of fluid in a downstream direction with respect to a direction of fluid flow through the vessel. A detector may also be provided for detecting a response signal transmitted from a probe region of the vessel positioned upstream of the first clamp. The response signal is related to the presence or absence of one or more target analytes in the vessel.

24 Claims, 13 Drawing Sheets

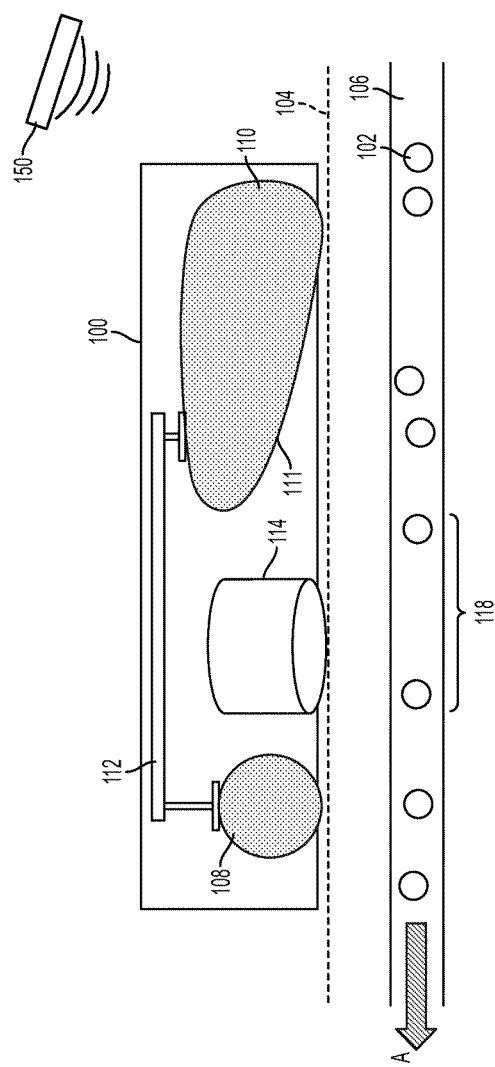

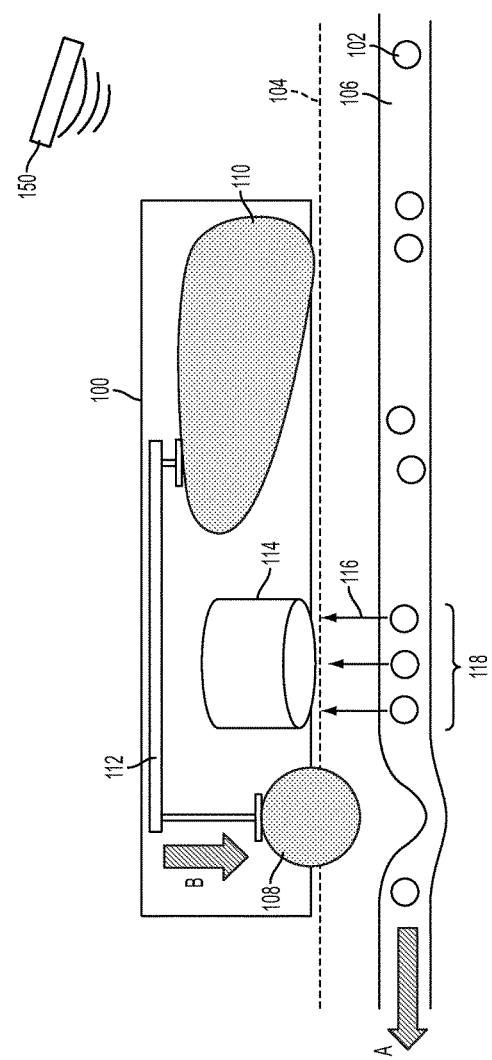

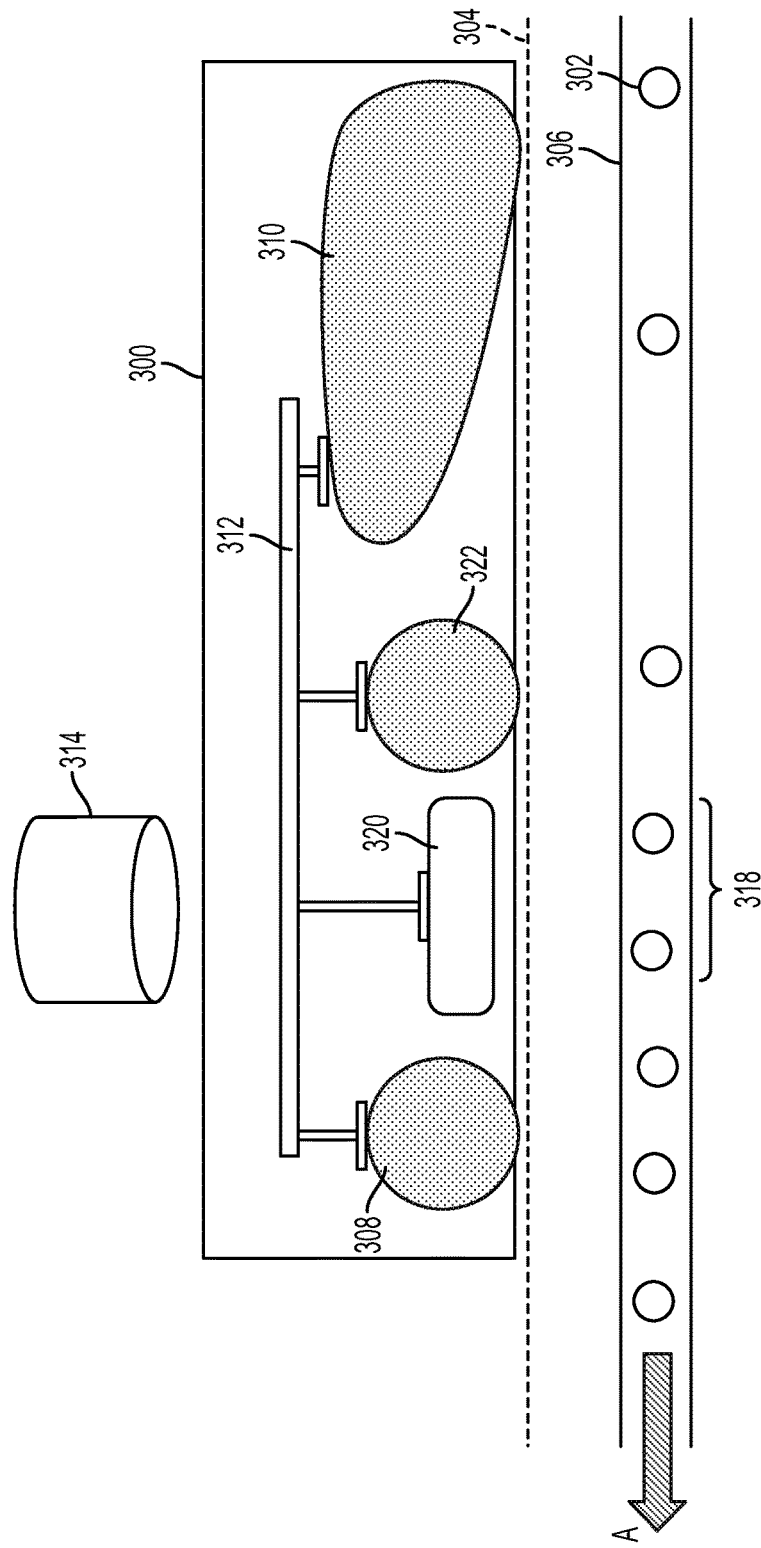

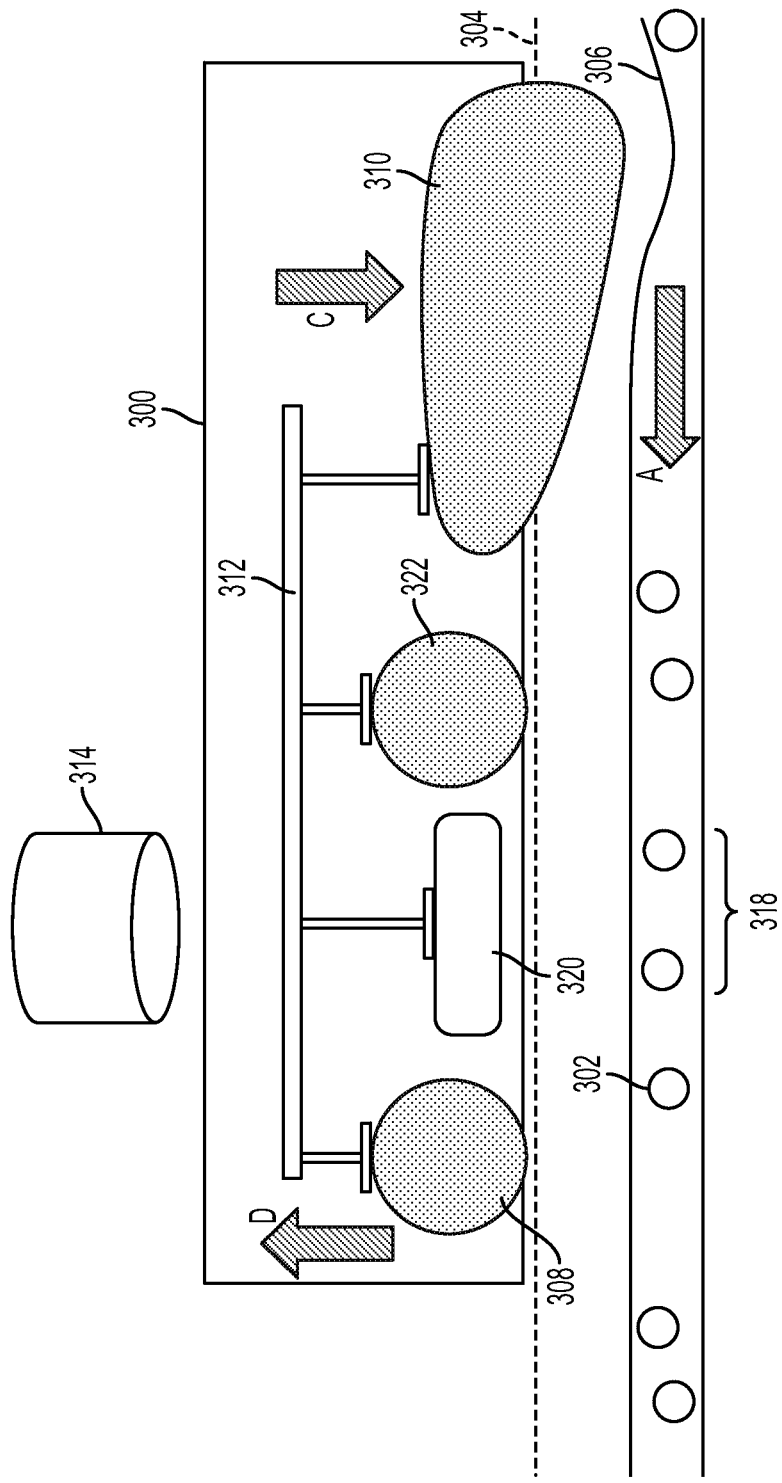

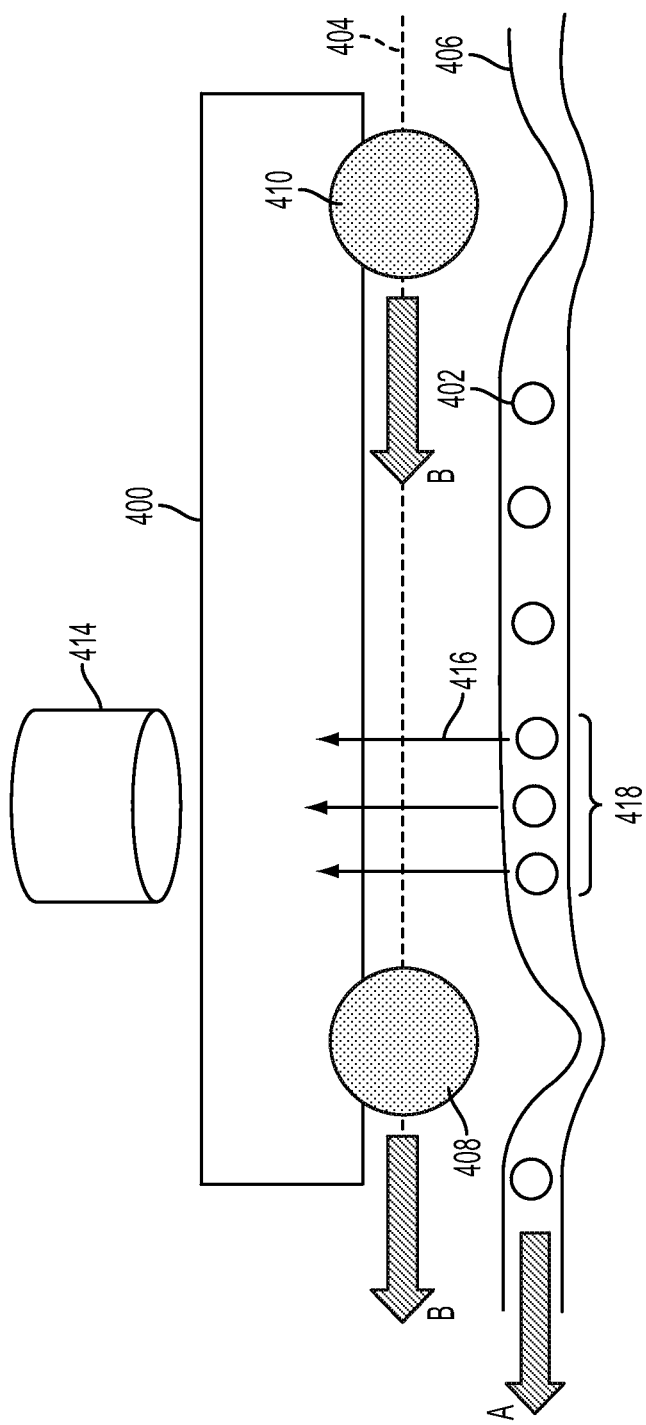

PULSATILE VENOUS BLOOD STOPPAGE FOR ANALYTE DETECTION

BACKGROUND

Unless otherwise indicated herein, the materials described in this section are not prior art to the claims in this application and are not admitted to be prior art by inclusion in this section.

A number of scientific methods have been developed in the medical field to detect and/or measure analytes of interest in a person's blood or other bodily fluids. Analytes of interest can include enzymes, reagents, hormones, proteins, cells or other molecules, such as carbohydrates, e.g., glucose. In a typical scenario, a person's blood is drawn and sent to a lab or input into a testing device, where one or more tests are performed to determine the presence or absence of an analyte of interest and/or measure the concentration of the analyte in the blood. However, some analytes are particularly difficult to identify and quantify with conventional sensing techniques. For small or rare analytes, such as circulating tumor cells, for example, only one such cell may be present in 10 mL of blood. Impractically large quantities of blood would have to be drawn or otherwise sampled and analyzed in order to detect such cells or estimate overall concentration in the blood with statistical significance.

Further, these rare or small analytes also present challenges for in vivo testing methods. Rare analytes will infrequently pass within the interrogation field of the detector and, even when they do, they may be difficult to detect. Because the in vivo signal obtained from the analyte of interest is typically weak in comparison to the background, many in vivo analyte detection and characterization techniques can suffer from a low signal-to-noise ratio (SNR). Low SNR can make discerning between target analytes present in the blood, versus other analytes, particles, and tissues, etc. very difficult, especially where the target analytes are rare in the blood or are of a relatively small size. Accordingly, rare analyte testing methods can be much more time consuming (if a large volume of blood must be analyzed), less sensitive, less specific and generally less informative.

SUMMARY

An apparatus for the in vivo detection of rare analytes of interest circulating in peripheral veins or other vessels by capturing such target analytes in a defined volume close to a surface of the body is provided. The apparatus may include one or more structures or clamps for inhibiting fluid flow, such as the flow of blood or lymph, in a portion of a vein or other vessel within a probe region. While blood flow is inhibited or stopped, a detector may interrogate the probe region and, if present, detect a response signal transmitted from one or more target analytes. Blood flow may be inhibited and the probe region interrogated over a plurality of probe times. In some examples, the apparatus may be provided as a wearable device.

Some embodiments of the present disclosure provide a wearable device including: (1) a mount configured to attach the wearable device to an external body surface proximate to a vessel; (2) a downstream clamp configured to be placed adjacent to an external body surface and apply a force to the vessel sufficient to inhibit a flow of fluid through the vessel beyond the downstream clamp; and (3) a detector configured to detect a response signal transmitted from a probe region of the vessel, wherein the probe region is positioned upstream of the downstream clamp with respect to a direction of fluid flow through the vessel, and wherein the response signal is related to presence or absence of one or more target analytes in the vessel.

Some embodiments of the present disclosure provide a method including: (i) applying, during a probe time, a force to a vessel with a first clamp sufficient to inhibit a flow of fluid through the vessel beyond the first clamp; and (ii) detecting, with a detector, a response signal transmitted from a probe region of the vessel during the probe time, wherein the probe region is positioned upstream of the first clamp with respect to a direction of fluid flow through the vessel, and wherein the response signal is related to presence or absence of one or more target analytes in the vessel.

Further embodiments of the present disclosure provide a method including: (i) during each of a plurality of probe times, applying a force to a vessel with a first clamp sufficient to inhibit a flow of fluid through the lumen beyond the first clamp; (ii) during each of the plurality of probe times, detecting with a detector a response signal transmitted from a probe region of the vessel, wherein the probe region is positioned upstream of the first clamp with respect to a direction of fluid flow through the vessel, and wherein the response signal is related to presence or absence of one or more target analytes in the vessel; and (iii) after each of the plurality of probe times, applying a force to the lumen with a second clamp sufficient to accelerate a volume of fluid in a downstream direction with respect to a direction of fluid flow through the vessel, wherein the second clamp is positioned upstream of the first clamp with respect to a direction of fluid flow in the vessel.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1A is a side, partial cross-sectional view illustrating operation of an example apparatus.

FIG. 1B is a side, partial cross-sectional view illustrating operation of the example apparatus of FIG. 1A.

FIG. 3A is a side, partial cross-sectional view illustrating operation of another example apparatus.

FIG. 3C is a side, partial cross-sectional view illustrating operation of the example apparatus of FIG. 3A.

FIG. 4 is a side, partial cross-sectional view illustrating operation of another example apparatus.

DETAILED DESCRIPTION

Figure 1C:
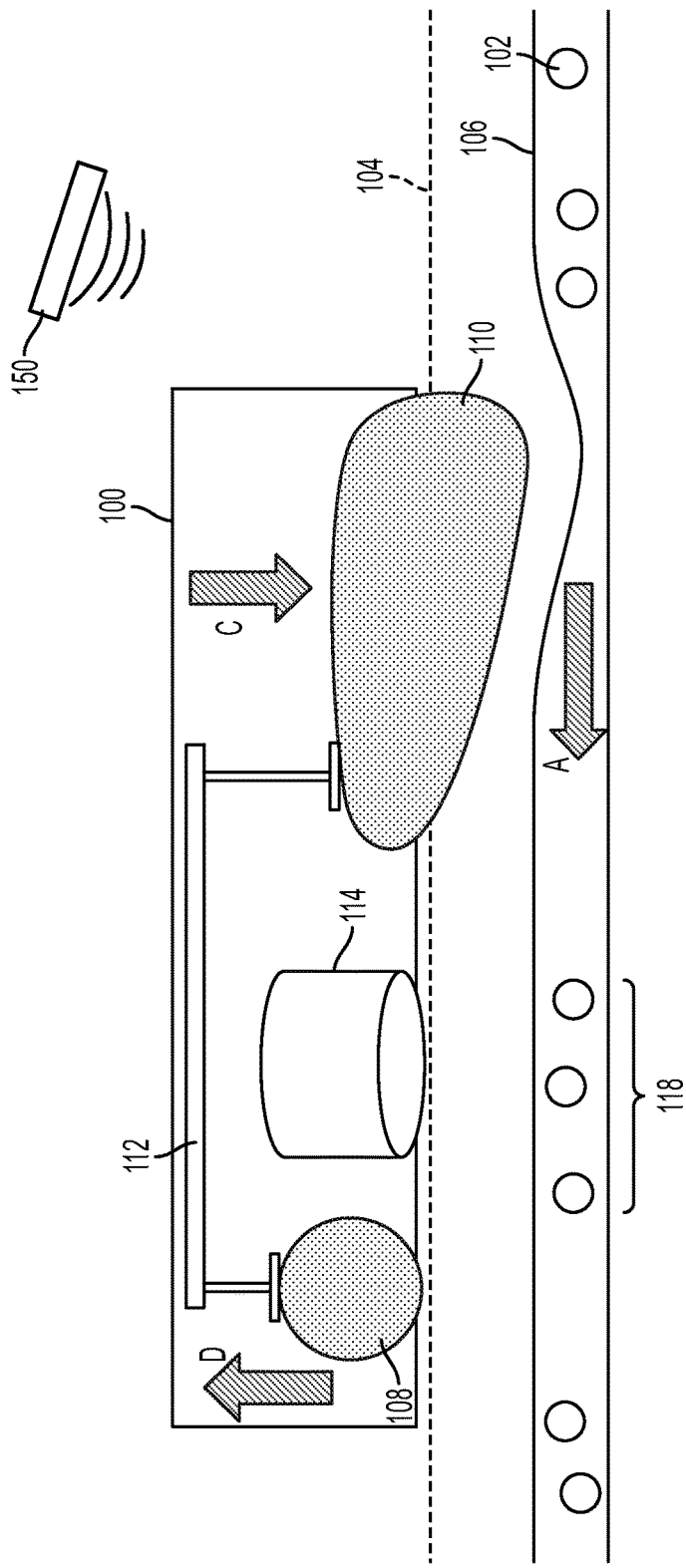
FIG. 1C is a side, partial cross-sectional view illustrating operation of the example apparatus of FIG. 1A.

Example methods and systems are described herein, making reference to the accompanying figures, which form a part of the disclosure. In the figures, similar symbols typically identify similar components, unless context dictates otherwise. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting and other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

One problem facing the in vivo detection of circulating rare particles in peripheral veins is that blood flow severely limits the time over which detection can occur. One approach to overcoming this problem is particle specific tagging with magnetic nanoparticles and subsequent capture to allow longer acquisition times for detection. However, magnetophoretic forces are small and long lengths of vein are needed over which a magnetic capture field exists to trap such a particle against a vein wall. As taught herein, in vivo detection of circulating rare particles may be facilitated by capturing or stopping particles of interest in a defined volume close to the surface of the body. To achieve this, blood flow in a peripheral vein thereby can be periodically stopped, thereby trapping particles of interest in a defined area. By periodically stopping venous flow—but maintaining the average blood throughput—particles of interest can be captured in a relatively short length of vein and, in some cases, attracted to a known probe site. Once blood flow is stopped, many different detection techniques may be utilized for detecting and quantifying the analyte(s) of interest, in vivo. For example, optical detection techniques, such as fluorescence detection, may be used.

An apparatus may be provided for periodically stopping blood flow in a vein. The apparatus may include at least one clamp and an actuator for applying a force to the vein with the clamp sufficient to inhibit blood flow. In some examples, the clamp may be positioned on and apply a force from an external body surface, such as the anterior surface of the wrist. The one or more clamps may be provided in a number of shapes and configurations, such as a cylindrical rod or bar, or a vertical plane or edge. The clamps may also be provided as or include a band or strap that goes around the circumference of a body surface. It may be desirable for the clamp to have a rounded edge where it comes in contact with the external body surface so as to not provide discomfort to the person under observation. Further, while many shapes and sizes are contemplated, the clamp should not be so small or thin that it may pierce through skin or tissue, but should not be so thick or wide that it may flatten a large area of the vein. For example, the clamp may have a width between 1 mm and 1 cm.

When the clamp is actuated, a volume of blood will accumulate or be "trapped" upstream of the clamp. In further examples, the apparatus may include two clamps, positioned along a vein and one positioned upstream of the other in the direction of blood flow. Clamping of the two clamps may be simultaneous or sequential, depending on the desired effect. For example, both clamps may be actuated simultaneously so as to "trap" a defined volume of blood between the clamps for interrogation. In some embodiments, the one or more clamps may also be movable along the length of the vein, for example by sliding or rolling, while continuing to apply a force to the vein.

The apparatus may also include a detector for noninvasively detecting and/or quantifying an analyte of interest in a probe region. Alternatively, the detector may be provided as a separate element. The detector may be positioned such that the probe region is upstream of the first (downstream) clamp. In a non-exhaustive list, the detector may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) detector. The detector may receive a response signal from the vein indicative of the presence, absence or concentration of an analyte of interest. In some cases, the apparatus may also include an excitation source, which may include any source for exciting an analyte of interest, or complex including analyte of interest, to generate a response signal. The excitation source may, for example, include a laser, light emitting diode, current source, voltage source, or magnetic field source.

The one or more clamps may be actuated for a certain probe time during which blood flow beyond the one or more clamps is inhibited and the probe region is interrogated by the detector. In some examples, the probe time may be adjusted by a feedback loop using the detector output. For example, if the detector output indicates that no analyte of interest was detected in the probe region during the probe time, then the duration of the probe time may be increased. By increasing the duration of the probe time, the probability that an analyte of interest will be detected is increased. The upper limit of the probe time may be dictated not only by health and safety considerations (stopping blood flow for too long may have adverse physiological effects), but also by the average blood throughput in the vein. The average blood throughput in a vein dictates the speed and volume of blood—and anything present in the blood, e.g., analytes—that passes through that vein. Thus, anything that reduces the average throughput will reduce the likelihood of finding a particle of interest in any given time within the probe region. In some embodiments, "slugs" or volumes of blood are sequentially driven past the probe region of vein after the probe period so that the average throughput is roughly the same as that for the unimpeded vein.

In further examples, magnetic tagging and capture of analytes of interest may be used in addition to blood flow inhibition or stoppage. Magnetic particles having an affinity for an analyte of interest may be introduced into circulation. The particles may be functionalized with a receptor or other moiety, such as an antibody, nucleic acid, aptamer, etc. If magnetic tagging is used, stopping blood flow allows magnetic capture to occur over a short length of vein, and further allows holding the particle at the vein wall during the blood refill phase (after the one or more clamps have been released).

While described in some example as being used to inhibit blood flow in a peripheral vein, it is contemplated that the apparatus described herein may be used to inhibit the flow of fluid through any type of vessel. For example, the apparatus may be used to concentrate and detect rare particles circulating in blood, urine, sweat, lymph, cerebrospinal fluid, digestive fluids, etc. The apparatus may inhibit the flow of fluid in a vein or vessel of another body system, including the lymphatic system, the digestive system, the nervous system, etc. In addition to applications inside of the body, the apparatus may further be used in many other applications to detect rare particles circulating in a fluid.

It should be understood that the above embodiments, and other embodiments described herein, are provided for explanatory purposes, and are not intended to be limiting. Variations on the above embodiments and other embodiments are possible, without departing from the scope of the invention as set forth by the claims.

II. Example Apparatus for Blood Flow Inhibition

One example of an apparatus 100 for non-invasively detecting one or more target analytes 102 in the body is shown in FIG. 1A. In this example, the apparatus 100 operates to periodically inhibit blood flow in a vein (or other lumen in the subsurface vasculature) such that one or more target analytes 102, if present, will aggregate and become concentrated within a portion of the vein, thereby increasing detectability of the analyte. The direction of blood flow is shown throughout the Figures with arrow A. The term "inhibit" as used herein is to be interpreted in the broadest possible sense to include a wide range of degrees of inhibition including from a complete stoppage of blood flow to any restraint or hindrance of blood flow sufficient to cause aggregation of one or more of the target analytes in the lumen, if present. The apparatus 100 may be positioned on an external portion of the body over a region of subsurface vasculature. In some cases, the apparatus 100 may be positioned over a portion of the body where the subsurface vasculature is relatively close to the skin surface or is otherwise readily accessible. For example, the apparatus may be placed on a skin surface 104 above a vein 106.

Figure 5A:
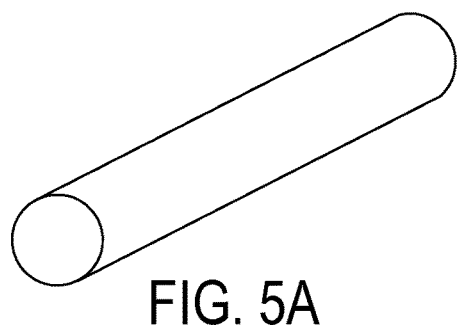
FIG. 5A is a perspective view of an example clamp for use in the apparatus of FIG. 1A-1C, 2, 3A-3C or 4.
Figure 5B:
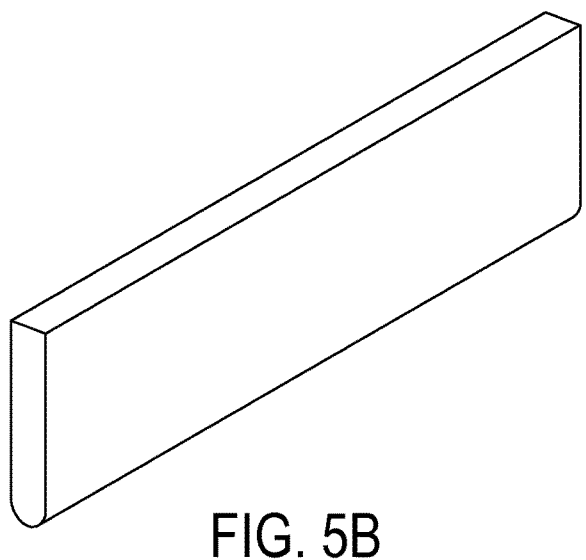
FIG. 5B is a perspective view of an example clamp for use in the apparatus of FIG. 1A-1C, 2, 3A-3C or 4.
Figure 5C:
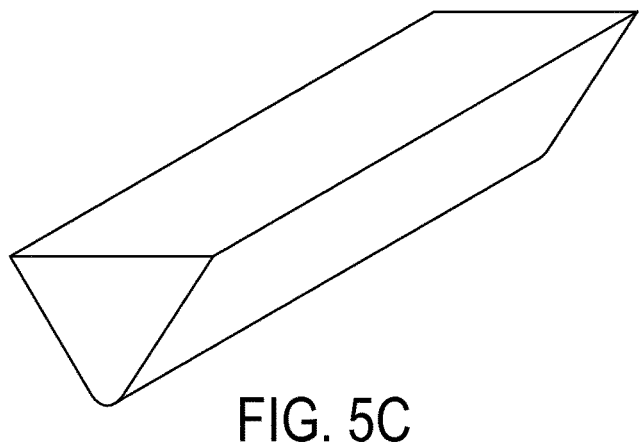
FIG. 5C is a perspective view of an example clamp for use in the apparatus of FIG. 1A-1C, 2, 3A-3C or 4.
Figure 6A:
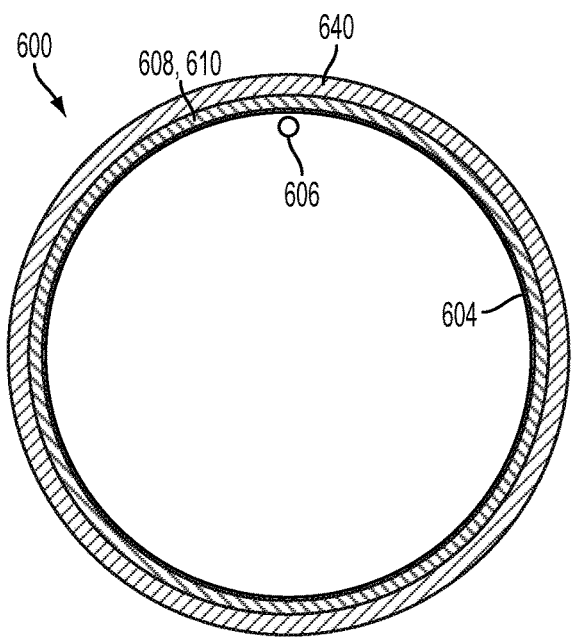
FIG. 6A is a cross sectional view of an example wearable device.
Figure 6B:
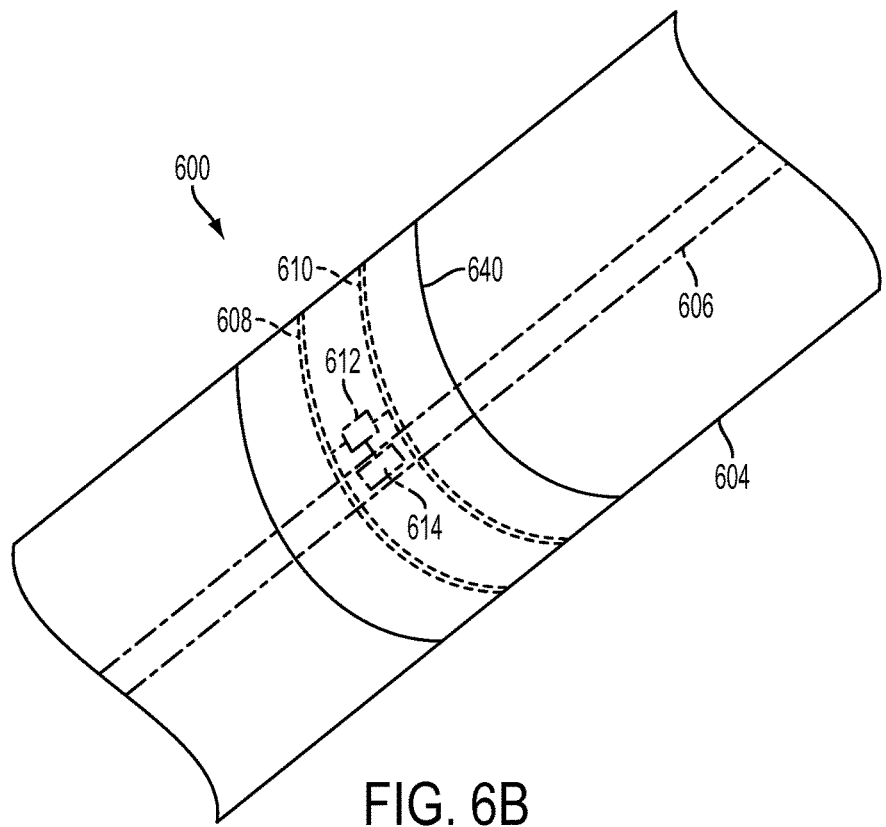
FIG. 6B is a perspective view of the example wearable device of FIG. 6A.

The apparatus 100 may include at least one clamp 108 for applying a force to a lumen of the subsurface vasculature, such as a vein 106. The clamp 108 may be of any size or shape. In some examples, as shown in FIGS. 5A-5C, the clamp 108 may be shaped as a cylindrical or triangular rod or a vertical plane. It may be desirable for the clamp to have a rounded edge where it comes in contact with the external body surface so as to not provide discomfort to the wearer or user of the apparatus 100. The clamp 108 may also be provided as or include a band or strap that goes around the circumference of a body surface, for example, as shown in FIGS. 6A and 6B. Further, the clamp 108 may be provided as an inflatable bladder. Generally, the clamp 108 may be sized and shaped such that it does not pierce through the skin or tissue when applying a force, but also so that it applies the force to a relatively narrow portion of a vein. The clamp 108 may, in some examples, have a width between 1 mm and 1 cm.

An actuator 112, operatively connected to the clamp 108, operates to actuate the clamp 108 towards (FIG. 1B), and subsequently away from (FIG. 1C), the vein 106. The actuator 112 is configured to actuate the clamp 108 to apply a force to the vein 106 sufficient to inhibit a flow of blood, in the direction of arrow A, beyond the clamp 108. The actuator 112 may be any type of actuator, including a hydraulic, pneumatic, electric or mechanical. Further, the actuator 112 may be adjusted to control the amount of force applied by the clamp 108 to the vein 106 which, in turn, will control the amount of blood flow inhibition achieved by the clamp 108.

A detector 114, configured to detect a response signal 116 (FIG. 1B) transmitted from a probe region 118 of the lumen of subsurface vasculature, may also be provided. The response signal 116 may be any signal related to the presence or absence of one or more target analytes 102 in the lumen of subsurface vasculature. The detector 114 may be any type of detector, including optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance). Accordingly, analyte response signal 116 may include any of an optical, acoustic, electrochemical, thermal, mechanical, magnetic or electromagnetic signal. For example, analyte response signal 116 may be an optical signal generated by a fluorescent property of the target analyte.

In some cases, an excitation source 150 may also be provided. As with detector 114, the excitation source may be provided on the apparatus 100, or may be external thereto, as shown in FIGS. 1A-1C. The excitation source 150 may be any source capable of emitting a signal that is benign to the wearer and results in a response signal that can be used to detect one or more target analytes. For example, the excitation source may be any of an electromagnetic, magnetic, optic, acoustic, thermal, or mechanical source. In one embodiment, the excitation source 150 may be an excitatory laser diode source that may induce an optical response signal 116. An excitation source is not necessary in all embodiments. For example, the response signal may be generated due to some inherent detectable property of the rare particles themselves.

The detector 114 may be provided as part of the apparatus 100, as shown in FIG. 1A, or it may be separate and remote from the apparatus 100 (e.g., as shown in FIG. 3A). Where the detector 114 is provided separately, the apparatus 100 may be secured on the skin 104 of a subject and brought into proximity with a remote detector 114 in order to detect the one or more target analytes in the body. In either case, the detector 114 is positioned such that the probe region 118 is positioned upstream of the clamp 108. The terms "downstream" and "upstream" are used in reference to the flow of blood (or other body fluid) through the lumen of subsurface vasculature, which is indicated by arrow A. Thus, as will be discussed further below, when the clamp 108 is actuated to apply a force to the vein 106, inhibiting the flow of blood, the target analytes 106 in the vein will congregate upstream of the clamp 108 and within the probe region 118. While the probe region 118 is illustrated in FIG. 1A as being located directly below the detector 114, it is contemplated that the probe region 118 may be positioned in any area where the detector 114 may receive a response signal.

In some examples, the apparatus 100 may also include a second clamp 110 positioned upstream of the first clamp 108. However, as will be described in detail below, the second clamp 110 is not required. The first 108 and second 110 clamps are positioned on the apparatus 100 such that they both lie longitudinally along the vein 106. Clamp 110 may be operably connected to the actuator 112, or it may be operably connected to a different actuator. In some examples, the second clamp 110 may be used to maintain an average throughput of blood through the vein 106. As described above, maintaining the average blood flow through the vein may help to maintain the likelihood and probability that a target analyte 102 will pass through the vein 106 (and the probe region 118) and be detected. To achieve this, the second clamp 110 may be configured to apply a force to the vein 106 sufficient to accelerate a volume of blood in a downstream direction. Accelerating a volume or "slug" of blood downstream may compensate for a reduction of instantaneous blood flow caused by actuation of the first clamp 108 against the vein 106. In some cases, the clamp 110 may be wedge-shaped and may be positioned such that a hypotenuse 111 of the wedge faces towards the vein 106 and downstream. In another embodiment the clamp 110 can pivot in a manner to strip blood in the lumen in a downstream direction. This shape, orientation, and movement may act to push a greater volume of blood towards the first clamp 108.

In operation, capture and detection of analytes of interest 102 using the apparatus 100 may proceed in phases. In the first phase ("Capture phase"), as shown in FIG. 1B, blood flow is inhibited in the vein 106 by actuating clamp 108 in the direction of arrow B. The volume of blood present in the probe region 118 of the vein is probed by detector 114 which receives a response signal 116 related to the presence or absence of one or more target analytes 102. Any detection technique, including fluorescence or photoacoustic techniques, may be used. An excitation source (not shown) may also be used to generate the response signal 116. In some examples, the probe region 118 can be approximately 1 mm in length.

By inhibiting blood flow, rare analytes of interest 102 present in the probe region 118 can be interrogated for extended times, allowing for enhanced signal to noise ratio as compared to the very short detection times achieved for particles in freely flowing blood. The probe time—the time during which blood flow is inhibited—may vary anywhere from 100 milliseconds to 10 seconds. The longer the probe time, the more reliable and precise the detection of an analyte of interest (due to increased integration time). However, increasing the probe time may decrease the likelihood that an analyte of interest will be captured in the probe region (due to the decrease in average throughput). Further, lengthy periods of blood inhibition or stoppage may have adverse physiological effects. Accordingly, the length of the probe time may be dictated by weighing the detection enhancements against not only the health and safety considerations, but also by the average blood throughput in the vein.

In some examples, it may be advantageous to stop the blood flow for time periods that are so long that it would not be possible to maintain an average flow rate equal to the unimpeded venous flow rate. This can be ameliorated by reducing the sample repetition rate (though still maintaining a higher average signal-to-noise ratio with respect to unimpeded flow). The probe time may be adjusted by a feedback loop (not shown) using the output from the detector 114. For example, if the detector output indicates that no analyte of interest was present in the probe region during the probe time, then the probe time may be increased.

Trapping or concentration of one or more analytes of interest in the probe region may be used, not only to detect and quantify an analyte, but also to remove, modify, destroy or otherwise render a target analyte inactive. The analytes targeted for removal, modification or destruction could be any substances or objects that, when present in the blood, or present at a particular concentration or range of concentrations, may affect a person's medical condition or the health. For example, the target analytes could include enzymes, hormones, proteins, cells or other molecules. Modifying or destroying the targets could include causing any physical or chemical change in the targets such that the ability of the targets to cause the adverse health effect is reduced or eliminated. For example, an energy sufficient to cause electrophoresis in, destroy, ablate or otherwise inactivate the target analyte may be transmitted into the probe region. Accordingly, the apparatus 100 may also include a signal source configured to transmit a signal into the probe region 118 sufficient to cause a physical or chemical change in a target analyte 102 present in the probe region 118. The physical or chemical change may reduce or eliminate the target analyte's ability to cause an adverse health effect As shown in FIG. 1C, when the detection cycle is completed, "slugs" or volumes of blood may be driven past the probe region 118 with the upstream clamp 110, thereby maintaining an average throughput roughly the same as that for the unimpeded vein. In this second phase ("Refill phase"), the upstream clamp 110 may be actuated in the direction of arrow C at the same time as the downstream clamp 108 is being released in the direction of arrow D. The wedge shape of the clamp 110 blocks upstream blood flow and forces venous blood downstream in the direction of arrow A, thereby accelerating a volume or "slug" of blood into the probe volume of the vein. Further, by providing a slight delay between activation of the upstream clam 110 and the downstream clamp 108, such that an increased volume of blood is captured in the region between the clamps, acceleration of the "slug" of blood may be further enhanced.

Figure 2:
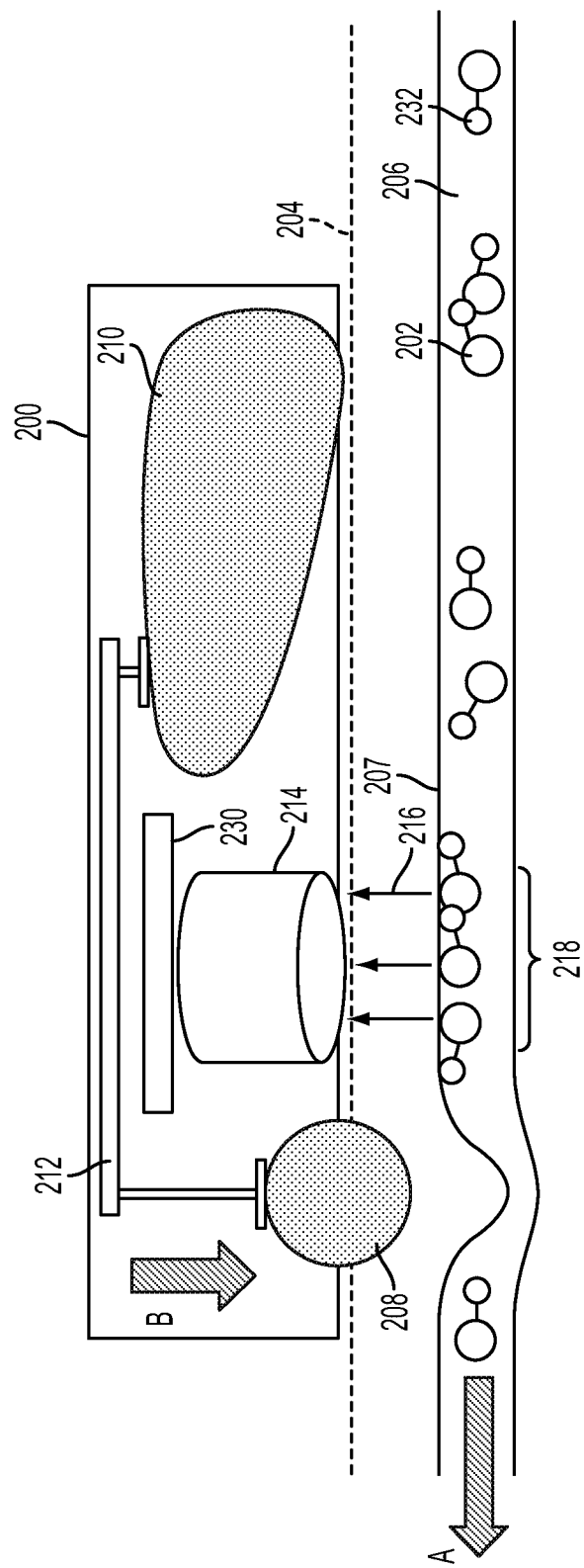
FIG. 2 is a side, partial cross-sectional view illustrating operation of another example apparatus.

Magnetic capture may also be used in some examples. In one arrangement, shown in FIG. 2, the apparatus 200 may include a magnet 230, in addition to clamps 208, 210, actuator 212 and detector 214. The magnet 230, which may be a strong magnet with a strong field gradient, can be used to attract target analytes 202 that have been tagged with a magnetic particle 232 near the proximal surface 207 of the vein via magnetophoretic forces. In operation, downstream clamp 208 may be actuated in the direction of arrow B, capturing one or more target analytes 202 in the probe region 218. Magnetic capture of magnetically tagged target analytes 202 may enhance sensitivity by drawing the magnetic particles 232 (and their bound analytes 202) to the proximal surface 207 of the vein in the probe region 218 and closer to detector 214. A response signal 216 may be detected by detector 214. In addition, because the magnetic particles 323 are held in the low flow velocity boundary layer adjacent to the vein wall, magnetic capture may also make it possible to hold onto any captured analytes of interest 202 during the vein refill phase, thereby increasing the integration time. Further, once the magnetic particles 232 have been pulled to the proximal surface 207 of the vein, they may be held there indefinitely by magnet 230 and interrogated. In this way, the device acts to physically "integrate" the signal, without integrating the noise. Magnetic particles 232 may be introduced into the body and be bound to target analytes 202 by conventional means.

The probe time in the case of magnetic capture may also be dictated by the time it takes a magnetically-bound target analyte to reach the proximal surface 207 of the vein. Characteristic times needed for magnetic capture on the proximal side 207 of the vein can be estimated based on the magnetic force and the viscous drag on representative tagged analytes. As an example, assuming 12 nm of $Fe_2O_3$ superparamagnetic nanoparticles having a saturation magnetic moment of $m_s = 3 \times 10^{-19}$ J T$^{-1}$ are used. These particles reach half their saturation magnetization at 26 mT. The magnetic force on N such particles is given by $Nm_sVB$, where the number of particles that correspond to one 1 μm particle is $(1\ \mu m/12\ nm)^3$, or approximately 579,000, and B is the modulus of the magnetic field. In a 100 mT field with a gradient of 100 mT mm$^{-1}$, the particles will be saturated and thus have a total force of 17.4 pN. The velocity that creates an equivalent Stokes drag force on a 10 μm diameter sphere (representing a cell, or other target analyte) in water at room temperature, is calculated to be 180 μm/s. Therefore, a cell, or other target analyte, attached to an equivalent of a 1 μm particle of ferromagnetic material might take approximately 5 seconds to move from the center of a 2 mm vein to the proximal edge 207.

Figure 3B:
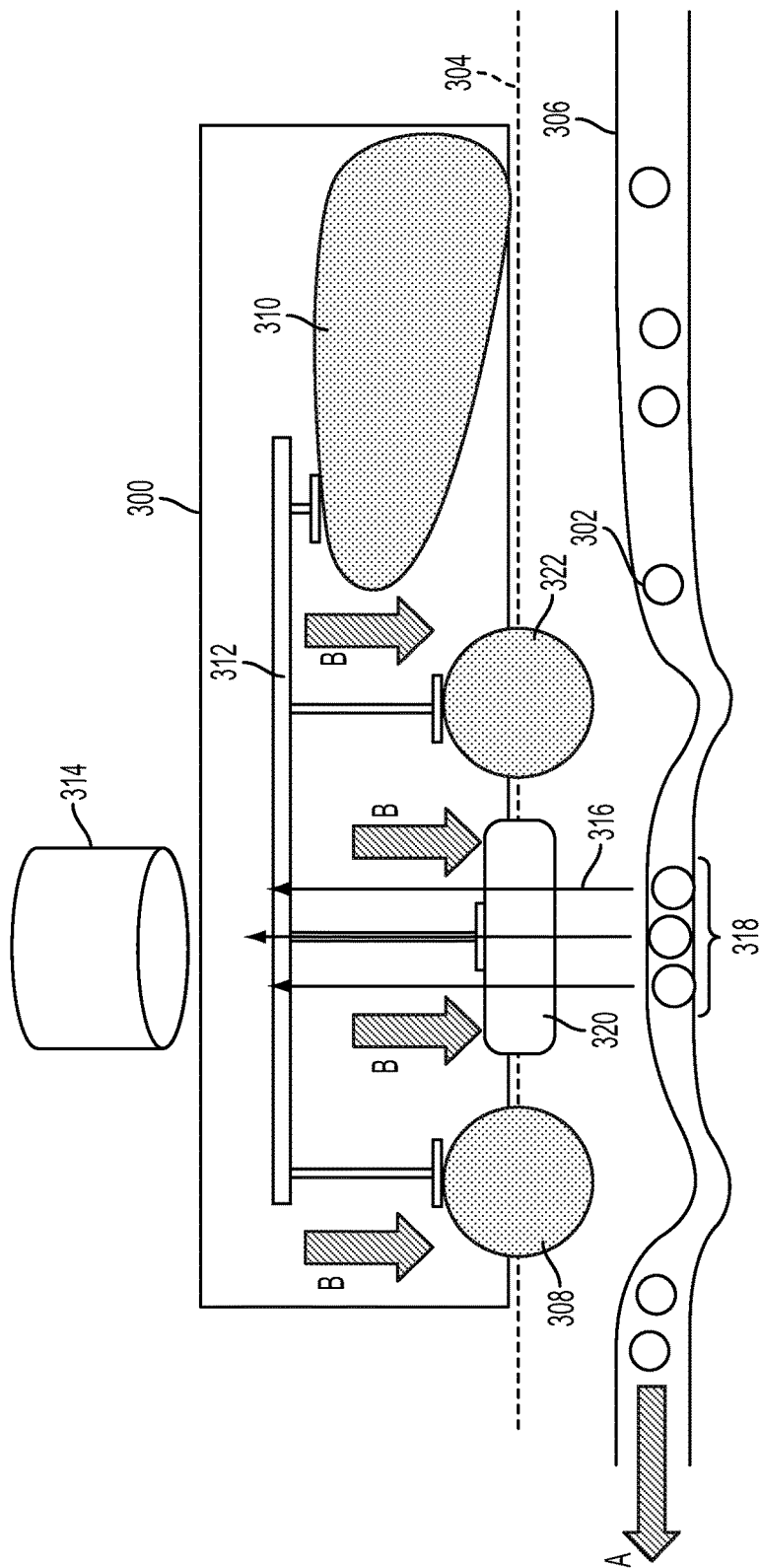
FIG. 3B is a side, partial cross-sectional view illustrating operation of the example apparatus of FIG. 3A.

Another example apparatus 300 is shown in FIGS. 3A-3C. In this embodiment, apparatus 300 may also include a plate 320 configured to be placed adjacent to the body surface 304. The plate 320 may be configured to compress the probe region 318 of the vein 306 positioned between a downstream clamp 308 and intermediary clamp 322 into a flattened volume. For example, in operation, clamp 308 can be actuated by actuator 312 followed by clamp 322, in the direction of arrows B as shown in FIG. 3B. Then plate 320 can be lowered to compress the probe region 318 of the vein 306. In response, the vein may expand laterally and compress vertically, as facilitated by the relatively low venous pressure (akin to compressing a garden hose filled with water). Any target analytes 306 present in the probe region are thereby confined to a smaller probe depth, which may enhance detectability. Additionally, thinning of the vein 306 and intervening tissue can allow stronger magnetic forces (if magnetic particles are used) as well as reduced optical scattering and absorption losses. The plate 320 may be of any size, shape or material. For example, the plate 320 may be between 1 mm and 2 cm on a side. In some examples, the plate 320 may also be curved to match the curvature of the body surface against which it is intended to be placed. The plate may be made transparent (by choice of material or geometry) to the response signal so as to not block the signal from reaching the detector. In addition, the plate geometry may be chosen to enhance the signal transduction from the analyte to the detector (for example, it might have light guiding or acoustic wave guiding properties).

As described with respect to FIGS. 1A-1C, the detector 314 may receive a response signal 316 from the probe region 318 related to the presence or absence of one or more target analytes 318. When the detection cycle is completed, the plate 320 may be released in the direction of arrow D. The upstream clamp 310 may then be actuated in the direction of arrow C at the same time as (or slightly before) the downstream clamp 308 and intermediate clamp 322 are released in the direction of arrow D, as shown in FIG. 3C. While three clamps 308, 310 and 322 are illustrated in this embodiment of apparatus 300, it is contemplated that fewer clamps may be used in capture of the one or more target analytes 306.

In a further example shown in FIG. 4, the apparatus 400 may include a first clamp 408 and a second clamp 410 configured to be movable in a downstream direction (arrows B) or upstream direction. The clamps 408, 410 may be actuated downwards toward the vein 406 such that they continue to apply a force to the vein while they are moved along the length of the vein on the body surface 404. In some examples, the clamps 408, 410 may be provided as rollers that roll along the body surface 404. The rollers can seal or otherwise compress downstream and upstream portions of the vein, defining a probe region 418 therebetween, and move or roll synchronously along the vein 406. The probe region 418, including any of the target analytes 402 trapped therein, may therefore be transported past the detector 414. A sequence of such rolling clamps can be used to define several sequential volumes that can be transported past the probe region 418 of the detector 414. The clamps 408, 410 may also be connected to a feedback loop (not shown) using the detector output. A response signal 416 indicating the presence or absence of an analyte of interest 402 in the probe region 418 can be fed back to the probes 408, 410 to stay stationary for extended probing of a given region of the blood. Further, blood volumes of interest between the probes 408, 410 may be manipulated in the upstream and downstream directions to make additional passes past the detector 414 and at different speeds. A magnetic capture mechanism may also be used in conjunction with blood stoppage and continuous transport.

The response signal 116, 216, 316, 416 may be used, as described herein to determine whether an analyte of interest is present in or absent from the probe region during a probe time. In addition, the response signal may be analyzed to quantify or determine a concentration of an analyte of interest in the blood, or other fluid. The presence, absence or concentration of an analyte of interest in the body may be indicative of a health state of the wearer or user of the device. Further, in some cases, if the response signal goes above or below a certain threshold, a notification, such as an alarm or visual alert, may be provided to the user or a physician.

III. Example Wearable Devices

FIGS. 6A-6B illustrate one embodiment of a wearable device 600. The wearable device 600 may include a mount 640 for mounting the wearable device 600 to an external body surface 604 proximate to a portion of subsurface vasculature, such as a vein 606. The mount 640 may allow the wearable device 600 to be mounted to or placed on any body surface. Blood flows in peripheral veins of the arm at approximately 3 cm/sec at an ambient pressure of approximately 5 mmHg (or approx. 0.1 psi). In general, venous pressure is far lower than arterial pressures. As veins of the arm are approximately 2 mm in diameter and lie ~2 mm below the anterior surface, the wearable device 600 may in some examples be mounted to a wrist. As shown in FIGS. 6A and 6B, the mount 640 may be a strap, but may also be provided as an adhesive, a necklace, a bracelet, eyewear, headwear, etc.

The wearable device 600 may also include at least some of the elements of apparatus 100, 200, 300 or 400 described above. For example, the wearable device 600 may include a first clamp 608 and a second clamp 610 operatively connected to an actuator 612. In some examples, a detector 614 may also be provided on the wearable device 600. However, it is contemplated that the detector 614 may be external to the wearable device 600. In such cases, the wearable device may be brought into proximity with an external detector which may receive a response signal transmitted from a probe region of the vein. The clamps 608, 610 may be provided as inflatable bladders or tubes which may run the full circumference of the mount 640, as shown in FIGS. 6A and 6B, or only a portion thereof. The actuator 612 may operate to inflate the clamps 608, 610, thereby applying a force to an external body surface 604 and, in turn, the vein 606.

Figure 7A:
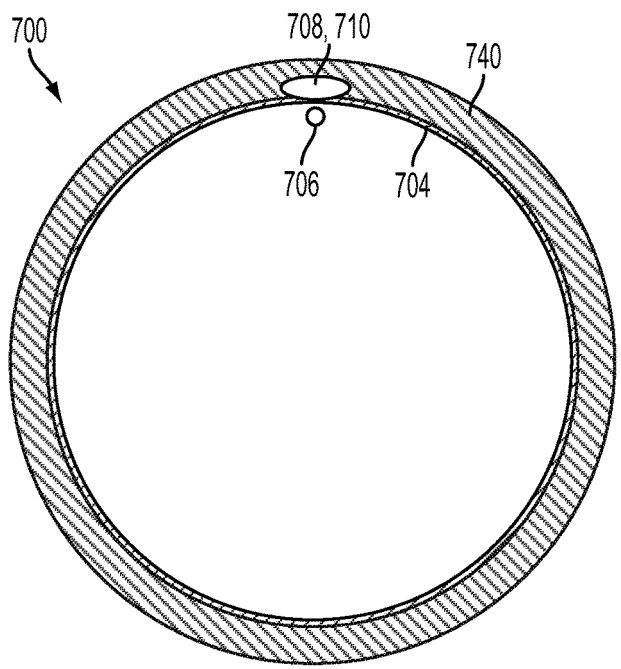
FIG. 7A is a cross sectional view of an example wearable device.
Figure 7B:
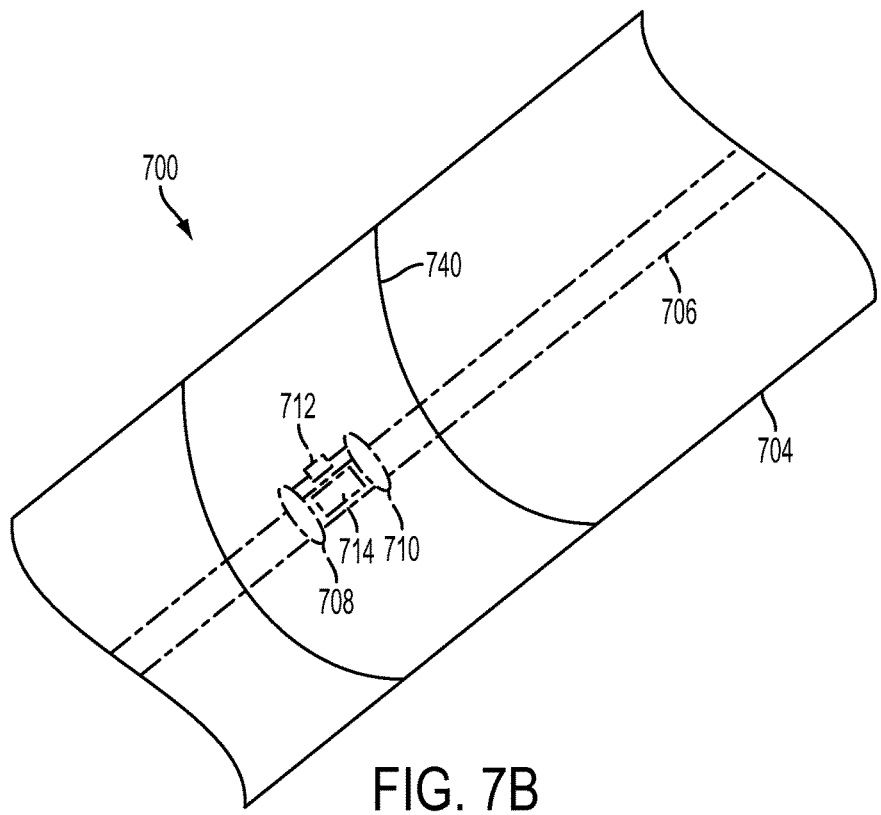
FIG. 7B is a perspective view of the example wearable device of FIG. 7A.

Another example of a wearable device 700, including a mount 740 for mounting the device to an external body surface 704 adjacent to a lumen of subsurface vasculature 706, first 708 and second 710 clamps connected to an actuator 712 and a detector 712, is shown in FIGS. 7A-7B. In this embodiment, clamps 708, 710 are illustrated as being ellipsoidal in shape, but may have any of the shapes illustrated in FIGS. 5A-5C or discussed herein.

VI. Illustrative Methods

Figure 8:
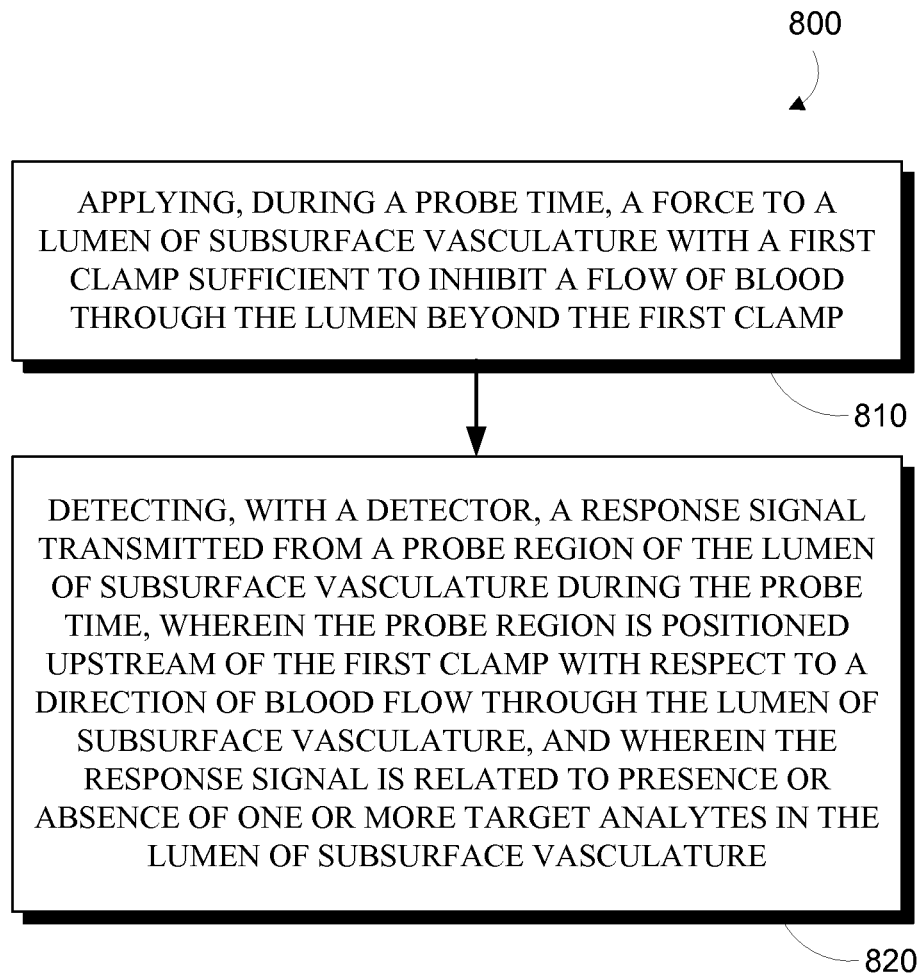
FIG. 8 is a flow chart of an example method.

FIG. 8 is a flowchart of a method 800 for detecting one or more target analytes present in a lumen of subsurface vasculature. The method may be practiced using an apparatus 100, 200, 300, 400 and/or a wearable device 600, 700 as described above. In a first step, a force is applied during a probe time to a lumen of subsurface vasculature with a first clamp. (810). The force applied by the first clamp is sufficient to inhibit a flow of blood through the lumen beyond the first clamp. A volume of blood, which may contain one or more target analytes, will therefore be "captured" or contained in a portion of the subsurface vasculature upstream (according to the direction of blood flow) of the first clamp. The clamp may apply the force to an external body surface adjacent to the lumen of subsurface vasculature.

A detector may detect a response signal transmitted from a probe region of the lumen of subsurface vasculature, the probe region being positioned upstream of the first clamp with respect to a direction of blood flow through the lumen of subsurface vasculature. (820). As described above, the detector may be any type of detector, including optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance). The response signal is related to the presence or absence of one or more target analytes in the lumen of subsurface vasculature and may include any of an optical, acoustic, electrochemical, thermal, mechanical, magnetic or electromagnetic signal. In some cases, the response signal may be generated, at least in part, by an excitation source, such as a source of optical or acoustic energy.

A second clamp may, in some examples, be provided to apply a force to the lumen sufficient to inhibit a flow of blood through the lumen beyond the second clamp, which is positioned upstream of the first clamp with respect to a direction of blood flow in the lumen of subsurface vasculature. The second clamp may have a similar shape to that of the first clamp and the two clamps may be used to define a fixed volume in the probe region. In some examples, a third clamp may also be provided, as shown in FIGS. 2A-2C for the purpose of accelerating a volume of blood past the probe region in order to maintain the average blood flow. In a further example, the probe region of the lumen of subsurface vasculature may also be compressed with a plate. As described above, compressing the probe region thins and also spreads the vein in that area, providing for enhanced detection of any target analytes present in the probe region.

In some embodiments, a second clamp may be provided upstream of the first clamp to apply a projected downstream force to the lumen sufficient to accelerate a volume of blood in a downstream direction with respect to a direction of blood flow through the lumen of subsurface vasculature. The second clamp may be wedge shaped. To enhance the acceleration of a volume of blood into the probe region, the force applied to the lumen by the first clamp may be released after applying the force to the lumen by the second clamp.

Figure 9:
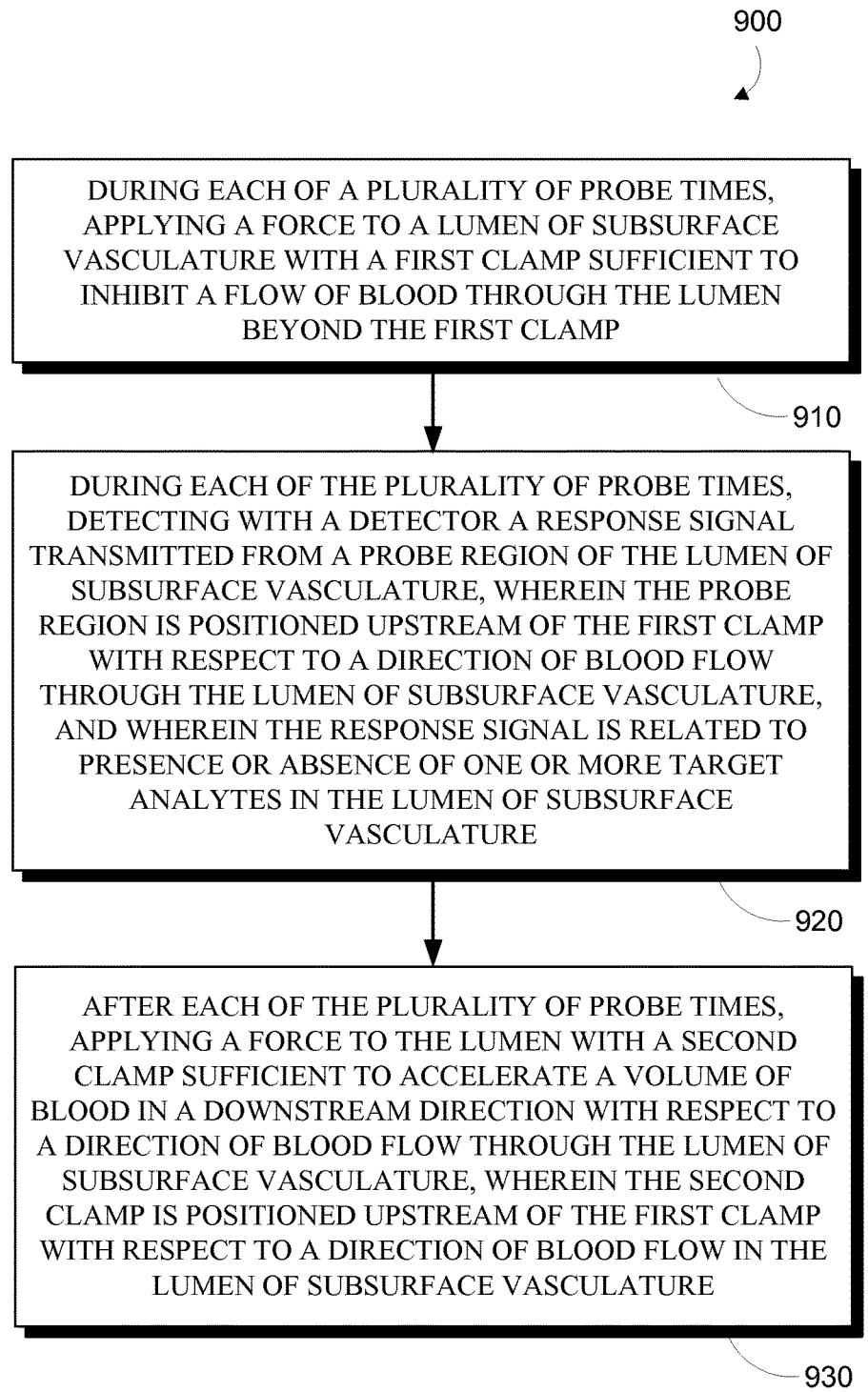
FIG. 9 is a flow chart of an example method.

Interrogation of the probe region may be repeated for multiple probe periods. FIG. 9 is a flowchart of another method 900 for detecting one or more target analytes present in a lumen of subsurface vasculature. The method may be practiced using an apparatus 100, 200, 300, 400 and/or a body-mountable device 600, 700 as described above. In a first step, a force is applied to a lumen of subsurface vasculature with a first clamp sufficient to inhibit a flow of blood through the lumen beyond the first clamp, during each of a plurality of probe times. (910). During each of the plurality of probe times, a response signal related to the presence or absence of one or more target analytes in the lumen of subsurface vasculature and transmitted from a probe region of the lumen is detected by a detector. (920). The probe region is positioned upstream of the first clamp with respect to a direction of blood flow. In a next step, a force is applied to the lumen with a second clamp, positioned upstream of the first clamp, sufficient to accelerate a volume of blood in a downstream direction after each of the plurality of probe times. In some examples, the force applied by the first clamp and the second clamp is applied to an external body surface adjacent to the lumen of subsurface vasculature. The force applied to the lumen with the second clamp is such that an average flow rate of blood through the lumen over the plurality of probe times is approximately equal to an unimpeded flow rate of blood through the lumen.

The duration of the probe time may be set based on a number of factors. The probe time, which includes the total time during which blood flow is inhibited and the time during which detection occurs, may in some examples be set based on a determination of a baseline noise level detected at the detector. The baseline noise level is dependent, at least in part, on the time period over which the response signal is integrated. For example, for a certain baseline noise level, if the integration time is set long enough, an analyte would be known to be detectable if present, with a certain degree of confidence. For some noise levels, there may be limit to how short the integration time may be set before a response signal is not detectable over the noise. Thus, the probe time may be set such that a response signal is detectable above the baseline noise level.

In some examples, the duration of the probe time may be increased if the analyte signal detected by the detector indicates the absence of the one or more target analytes in the probe region during the probe time. The duration of the probe time may also be increased if the analyte signal detected by the detector indicates the presence of the one or more target analytes in the probe region in an amount below a set threshold. By increasing the duration of the probe time, detection sensitivity may be increased due to the increased integration time and it may be more likely that one or more target analytes will enter the probe region and be detected by the detector. However, this increased sensitivity and likelihood of capture must be weighed against the reduced blood throughput in setting the length of the probe time. Moreover, if the probe time is so long (or the concentration of the target analyte is sufficiently high) that the sensitivity of the detector is exceeded, the probe time may be reduced. Accordingly, the duration of the probe time may be decreased if the analyte signal detected by the detector indicates the presence of the one or more target analytes in the probe region in an amount above a set threshold.

V. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location). In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and how it may be used.

What is claimed is:

1. A wearable device, comprising:
a mount for attaching the wearable device to an external body surface proximate to a vessel having a fluid flowing therethrough;
a downstream clamp, positioned on the mount, that is configured to apply a downward force to the vessel sufficient to inhibit a flow of the fluid through the vessel beyond the downstream clamp, with respect to a direction of fluid flow through the vessel;
an upstream clamp, positioned on the mount upstream of the downstream clamp, that is configured to apply a downward force to the vessel sufficient to inhibit a flow of fluid through the vessel beyond the upstream clamp, with respect to the direction of fluid flow through the vessel; and
a detector, positioned between the downstream clamp and the upstream clamp, that can detect a response signal transmitted from a probe region of the vessel, wherein the probe region is positioned between the downstream clamp and the upstream clamp, and wherein the response signal is indicative of one or more target analytes in the vessel.

2. The wearable device of claim 1, wherein the upstream clamp is configured to apply a force to the vessel sufficient to accelerate a volume of fluid in a downstream direction with respect to a direction of fluid flow through the vessel.

3. The wearable device of claim 2, wherein the upstream clamp is wedge-shaped.

4. The wearable device of claim 3, wherein the upstream clamp is oriented such that a hypotenuse of the wedge faces towards the vessel and downstream with respect to the direction of fluid flow in the vessel when attached to a subject.

5. The wearable device of claim 1 further comprising a plate configured to be placed adjacent to the body surface and further configured to compress a probe region of the vessel positioned between the downstream clamp and upstream clamp.

6. The apparatus of claim 2, wherein the downstream clamp and upstream clamp are movable in a downstream or upstream direction with respect to the direction of fluid flow in the vessel while continuing to apply a force to the vessel.

7. The wearable device of claim 1, further comprising at least one actuator, configured to:
actuate the downstream clamp to apply a force to the vessel.

8. The wearable device of claim 1, further comprising a magnetic field source configured to attract one or more magnetic particles present in the vessel towards a proximal inner surface of the vessel.

9. A method, comprising:
applying, during a probe time, a force to a vessel with a first clamp sufficient to inhibit a flow of fluid through the vessel beyond the first clamp;
detecting, with a detector, a response signal transmitted from a probe region of the vessel during the probe time, wherein the probe region is positioned upstream of the first clamp with respect to a direction of fluid flow through the vessel, and wherein the response signal is indicative of one or more target analytes in the vessel;
after the probe time, while maintaining the force applied to the vessel by the first clamp, applying a force to the vessel with a second clamp sufficient to inhibit a flow of fluid through the vessel beyond the second clamp, wherein the second clamp is positioned upstream of the first clamp with respect to the direction of fluid flow in the vessel; and
after applying the force to the vessel with the second clamp, releasing the force applied to the vessel by the first clamp;
wherein the detector is positioned between the first clamp and the second clamp.

10. The method of claim 9, wherein the force is applied to an external body surface adjacent to the vessel.

11. The method of claim 9, further comprising:
during the probe time applying a force to the vessel with the second clamp sufficient to inhibit a flow of fluid through the vessel beyond the second clamp.

12. The method of claim 9, further comprising:
compressing the probe region of the vessel with a plate positioned between the first clamp and the second clamp.

13. The method of claim 9, further comprising:
applying a force to the vessel with the second clamp sufficient to accelerate a volume of fluid in a downstream direction with respect to a direction of fluid flow through the vessel.

14. The method of claim 9, further comprising:
determining that the response signal detected by the detector during the probe time indicates absence of the one or more target analytes in the probe region; and
in response to the determining, increasing a duration of the probe time.

15. The method of claim 9, further comprising:
determining that the response signal detected by the detector during the probe time indicates presence of the one or more target analytes in the probe region in an amount below a set threshold; and
in response to the determining, increasing a duration of the probe time.

16. The method of claim 9, further comprising:
determining that the response signal detected by the detector during the probe time indicates presence of the one or more target analytes in the probe region in an amount above a set threshold; and
in response to the determining, decreasing a duration of the probe time.

17. The method of claim 9, further comprising:
applying to the probe region a signal sufficient to cause a physical or chemical change in the one or more target analytes present in the probe region, wherein the physical or chemical change reduces or eliminates the target analyte's ability to cause an adverse health effect.

18. A method, comprising:
during each of a plurality of probe times, applying a force to a vessel with a first clamp sufficient to inhibit a flow of fluid through the vessel beyond the first clamp;

during each of the plurality of probe times, detecting with a detector a response signal transmitted from a probe region of the vessel, wherein the probe region is positioned upstream of the first clamp with respect to a direction of fluid flow through the vessel, and wherein the response signal is related to one or more target analytes in the vessel; and after each of the plurality of probe times, while maintaining the force applied to the vessel by the first clamp, applying a force to the vessel with a second clamp sufficient to accelerate a volume of fluid in a downstream direction with respect to a direction of fluid flow through the vessel, wherein the second clamp is positioned upstream of the first clamp with respect to the direction of fluid flow in the vessel;

wherein the detector is positioned between the first clamp and the second clamp.

19. The method of claim 18, further comprising: applying the force to the vessel with the second clamp such that an average flow rate of fluid through the vessel over the plurality of probe times is approximately equal to an unimpeded flow rate of fluid through the vessel.

20. The method of claim 18, wherein the force applied by the first clamp and the force applied by the second clamp are applied to an external body surface adjacent to the vessel.

21. The method of claim 18, further comprising:
determining that the response signal detected by the detector during a particular probe time indicates absence of the one or more target analytes in the probe region; and
in response to the determining, increasing a duration of the particular probe time.

22. The method of claim 18, further comprising:
determining that the response signal detected by the detector during a particular probe time indicates presence of the one or more target analytes in the probe region in an amount below a set threshold; and
in response to the determining, increasing a duration of the particular probe time.

23. The method of claim 18, further comprising:
determining that the response signal detected by the detector during a particular probe time indicates presence of the one or more target analytes in the probe region in an amount above a set threshold; and
in response to the determining, decreasing a duration of the probe time.

24. The method of claim 18, further comprising applying to the probe region a signal sufficient to cause a physical or chemical change in the one or more target analytes present in the probe region, wherein the physical or chemical change reduces or eliminates the target analyte's ability to cause an adverse health effect.

* * * * *